United States Patent [19]

Kato et al.

[11] Patent Number: 5,292,923

[45] Date of Patent: Mar. 8, 1994

[54] METHOD OF PREPARING α-L-ASPARTYL-L-PHENYLALANINE METHYL ESTER HYDROCHLORIDE

[75] Inventors: Toshihisa Kato; Shinichi Kishimoto; Hideo Takeda; Mikiya Kano; Tadashi Takemoto, all of Kawasaki, Japan

[73] Assignee: Ajinomoto Co., Inc., Tokyo, Japan

[21] Appl. No.: 886,101

[22] Filed: May 21, 1992

[30] Foreign Application Priority Data

May 23, 1991 [JP] Japan .................... 3-221332

[51] Int. Cl.$^5$ ........................... C07C 229/00
[52] U.S. Cl. ........................ 560/40; 560/41; 562/450
[58] Field of Search ............ 560/40, 41; 562/450

[56] References Cited

U.S. PATENT DOCUMENTS

| | | |
|---|---|---|
| 3,786,039 | 1/1974 | Ariyoshi et al. |
| 3,933,781 | 1/1976 | Bachman et al. |
| 4,173,562 | 11/1979 | Bachman et al. |
| 4,550,180 | 10/1985 | Takemoto et al. |
| 4,680,403 | 7/1987 | Hisamitsu et al. |
| 4,684,745 | 8/1987 | Takemoto et al. ............ 560/41 |
| 4,778,916 | 10/1988 | Mita et al. ............ 560/40 |
| 4,801,732 | 1/1989 | Mita et al. ............ 560/40 |

FOREIGN PATENT DOCUMENTS

| | | | |
|---|---|---|---|
| 1187075 | 5/1985 | Canada ................ 560/41 |
| 0127977 | 12/1984 | European Pat. Off. ........ 560/41 |
| 0128694 | 12/1984 | European Pat. Off. ........ 560/41 |

Primary Examiner—José G. Dees
Assistant Examiner—Keith MacMillan
Attorney, Agent, or Firm—Oblon, Spivak, McClelland, Maier & Neustadt

[57] ABSTRACT

A method of preparing α-L-aspartyl-L-phenylalanine methyl ester hydrochloride (α-APM.HCL) from a reaction mixture of N-formyl-L-aspartic acid anhydride and L-phenylalanine methyl ester (PM), wherein α-APM.HCl is produced without isolating an intermediate by solid-liquid separation during the course of the reaction process.

9 Claims, No Drawings

METHOD OF PREPARING α-L-ASPARTYL-L-PHENYLALANINE METHYL ESTER HYDROCHLORIDE

BACKGROUND OF THE INVENTION

1. Field of the Invention

The present invention relates to methods in general, and in particular to industrial scale methods, of preparing α-L-aspartyl-L-phenylalanine methyl ester hydrochloride (hereinafter referred to as "α-APM.HCl").

2. Discussion of the Background

α-APM is a dipeptide sweetener having a sweetness of about 200 times that of sucrose (cane sugar). Because of its extremely good sweetening properties and its low caloric value, it has been used significantly as a diet sweetener. It is expected that the wordwide demand for α-APM will exceed 10,000 tons before 1995.

α-APM.HCl may be prepared by a method in which water is added to a reaction mixture (either in the form of a solution or a suspension) of an organic solvent containing N-formyl-α-L-aspartyl-L-phenylalanine methyl ester (hereinafter referred to as "F-α-APM"). The resultant mixture is heated, extracted with water and the resultant two layers are separated. N-formyl-α-aspartyl-L-phenylalanine methyl ester which remains dissolved in the separated aqueous layer is then deformylated and the α-L-aspartyl-L-phenylalanine methyl ester (hereinafter referred to as "α-APM") formed is crystallized out as its hydrochloride salt, and isolated.

Previous methods of producing α-APM.HCl include:

(i) a method of producing α-APM as its hydrohalide salt after deprotecting an N-protected-α-L-aspartyl-L-phenylalanine methyl ester which is formed by a condensation of N-protected-L-aspartic anhydride and L-phenylalanine methyl ester (hereinafter referred to as "L-Phe-OMe" or "PM"); and (ii) a method of producing α-APM as its hydrohalide salt after deprotecting an N-protected-α-L-aspartyl-L-phenylalanine which is formed by condensation of an N-protected-L-aspartic acid anhydride and L-phenylalanine (hereinafter referred to as "L-Phe") followed by methyl-esterifying the deprotected product.

One example of method (i) is described in U.S. Pat. No. 3,786,039. The condensation reaction is carried out in an organic solvent, followed by evaporative removal of the organic solvent, isolation of the resulting F-α-APM or its PM salt as a solid, and finally deprotecting the formulated product to yield o-APM.HCl. This method, however, requires the isolation of the intermediate F-α-APM. Due to the complications and additional required steps for isolating this intermediate, this method is not suitable for industrial application.

One example of method (ii) is described in U.S. Pat. No. 3,933,781. N-formyl-α-L-aspartyl-L-phenylalanine (hereinafter referred to as "F-α-AP") is formed by condensing N-formyl-L-aspartic acid anhydride and L-Phe in glacial acetic acid, followed by removal of the formyl group from the product to form α-L-aspartyl-L-phenylanine (hereinafter referred to as "α-AP"), isolation of the α-AP intermediate and finally esterification of the isolated intermediate to obtain α-APM.HCl. As with the other previously described method, this method also suffers the disadvantaqe of requiring isolation of an intermediate compound.

Similarly, U.S. Pat. No. 4,173,562 illustrates a method of obtaining α-APM.HCl by esterifying isolated F-α-AP or α-AP with hydrochloric acid and methanol.

Japanese Patent Application Laid-Open No. 61-143397 illustrates a method of preparing F-α-AP by condensing N-formyl-L-aspartic acid anhydride and L-Phe in water. In accordance with the method, it is also necessary to isolate F-α-AP and to deprotect and esterify it to obtain α-APM.HCl. Therefore, the method is also defective for industrial use.

In all of the above methods, F-α-AP or α-AP must be isolated during the procedure. In view of the complications and additional required steps for isolation of these intermediates, these methods are not suitable industrial methods. There is accordingly a need for methods not suffering the above disadvantages.

SUMMARY OF THE INVENTION

The objects of the present invention include providing a simple method of obtaining α-APM.HCl without requiring the isolation of an intermediate by solid-liquid separation from the reaction mixture of N-formyl-L-aspartic anhydride and PM during the course of the reaction procedure. More specifically the present invention obviates the problem in the prior art which necessitates the isolation of an intermediate by solid-liquid separation during the course of the reaction of obtaining α-APM.HCl, necessitating the use of additional devices for the isolation and the carrying out of complicated operations when carrying out the prior art methods on an industrial scale.

In order to overcome this drawback, the present inventors earnestly investigated and, as a result, have surprisingly found that F-α-APM can be extracted from a reaction solution of N-formyl-L-aspartic anhydride and PM with water having a temperature of from 40° C. to 80° C. and further, that deprotection and crystallization by adding hydrochloric acid and methanol to the resulting aqueous solution directly yields α-APM.HCl. On the basis of the findings, they have achieved the present invention which overcomes the problems encountered in the prior art methods.

In accordance with the present invention which is particularly advantageously practiced on an industrial scale, α-APM.HCl may be directly obtained from a reaction mixture of F-α-APM (which may contain F-α-APM as an impurity) without isolating the intermediate by solid-liquid separation during the course of the reaction process. Therefore, the method of the present invention needs neither devices for solid-liquid separation nor complicated operation for the separation, and it is therefore extremely advantageous from an industrial viewpoint.

DETAILED DESCRIPTION OF THE PREFERRED EMBODIMENTS

More precisely, the condensation of N-formyl-L-aspartic anhydride and PM may be carried out in an organic solvent, in accordance with the processes described in U.S. Pat. Nos. 3,786,039 and 4,680,403, both of which are incorporated herein by reference. Suitable examples of organic solvents for the condensation reaction, include but are not limited to N,N-dimethylformamide, acetic acid, halogenated hydrocarbons (such as ethylene dichloride, dichloromethane, or chloroform), acetates (such as methyl acetate or ethyl acetate), hydrocarbons (such as toluene or xylene), and mixtures of these.

N-formyl-L-aspartic acid anhydride which is used as the starting material in the present invention may be produced industrially advantageously by the method described in U.S. Pat. No. 4,550,180, which is incorporated herein by reference.

PM, which is the other starting material of the present invention, may be produced also industrially advantageously by esterifying L-Phe with sulfuric acid and methanol, followed by extracting the product into an organic solvent and removing unreacted methanol from the resulting organic solution to yield an organic solvent solution of PM. (U.S. Pat. No. 4,880,403)

The reaction is conducted by dissolving or suspending N-formyl-L-aspartic acid anhydride in an organic solvent, to which an organic solvent solution of PM is added. The reaction temperature is maintained between 0° C. and 50° C., and preferably within a range of from 5° C. to 30° C.

The reaction time is not specifically defined.

The organic solvent to be used may be selected from the solvents for the condensation reaction mentioned hereinabove. Preferably, acetic acid is used as the solvent for dissolving N-formyl-L-aspartic acid anhydride and toluene is used as the solvent for dissolving PM.

From the practical viewpoint, the concentration of acid anhydride used in the reaction is from 0.1 to 1.5 mol/liter, preferably from 0.5 to 1.1 mol/liter. The concentration of PM used is from 0.1 to 1.2 mol/liter, preferably from 0.5 to 0.8 mol/liter. After the condensation reaction, the concentration of F-α-APM is from 0.1 to 0.9 mol/liter, preferably from 0.3 to 0.6 mol/liter.

F-α-APM, as formed, may precipitate out of solution during the reaction, depending upon its concentration, to give a suspension. This, however, causes no harmful influence on subsequent operations.

Warm water or cold water is added to the reaction solution and then heated. The resulting mixture is stirred at a temperature of from 40° C. to 80° C. then allowed to separate into two layers, whereupon the desired product, F-α-APM, is found in the aqueous layer. The amount of water to be added for the extraction is not specifically defined, provided that it is sufficient for extraction and layer separation. From a practical viewpoint, it may be at most from 30 wt.% to 400 wt.% of the amount of F-α-APM formed.

Where the reaction is carried out in an acetic acid/toluene mixed solvent system, it is desirable to remove the acetic acid from the reaction mixture by concentration with an addition of toluene. This allows the F-α-APM to be extracted into the separated aqueous layer more effectively.

The conditions for removing acetic acid by concentrating the reaction mixture with an addition of toluene varies in accordance with the organic solvent in which PM is dissolved. In general, the removal of acetic acid may be carried out at a pressure of from 10 to 760 Torr and at a temperature of 90° C. or lower. However, since concentration at a high temperature accelerates the decomposition of F-α-APM, it is preferable that the temperature be maintained at 60° C. or lower.

The aqueous solution of F-α-APM thus obtained is treated with methanol and hydrochloric acid and then crystallized, for example, by the method illustrated in U.S. Pat. No. 4,684,745 which is incorporated herein by reference, to isolate α-APM.HCl.

In general, after the condensation reaction, the reaction mixture also contains N-formyl-β-L-aspartyl-L-phenylalanine methyl ester (hereinafter referred to as "F-β-APM") in an amount of from 5 wt.% to 35 wt.% of the desired product, F-α-APM. Also in this case, the extraction may be performed in the same manner as above and α-APM.HCl can be isolated. The β-isomer may be separated from the α-isomer in the next APM.HCl crystallization step, and therefore, the desired α-APM.HCl isolated with no trouble.

Obviously, numerous modifications and variations of the present invention are possible in light of the above teachings. It is therefore to be understood that within the scope of the appended claims, the invention may be practiced otherwise than as specifically described herein.

EXAMPLES

Example 1:

50 g of water was added to a mixed solvent comprising 25 g of acetic acid and 100 g of toluene containing 20 g of F-α-APM and the mixture heated to 60° C. After stirring minutes, the mixture was left static for 30 minutes to form two separate layers, and the aqueous layer subsequently isolated.

To the aqueous layer were added 10 ml of 35% hydrochloric acid and 10 ml of methanol, and the whole was heated at 60° C. for 20 minutes for deformylation. After cooling, 25 ml of 35% hydrochloric acid was added further, and the whole was stirred for 2 days at 20° C. for crystallization. Then, it was stirred at 5° C. for an additional 3 hours. The crystals precipitated out were isolated to obtain 12.2 g of crude wet α-APM.

These were analyzed by an amino acid analyzer and high performance liquid chromatography and were found to contain 8.0 g of α-APM, 0.3 g of α-APM2 and 0.52 g of α-AP. The yield of α-APM hydrochloride based on F-α-APM was 44%.

Example 2:

50 g of water was added to a mixed solvent comprising 25 g of acetic acid and 100 g of toluene containing 20 g of F-α-APM and 4.3 g of F-β-APM, and the mixture was heated to 50° C. After stirring for 15 minutes, the mixture was left static for 30 minutes to form two separate layers, and the aqueous layer subsequently isolated.

To the aqueous layer were added 10 ml of 35% hydrochloric acid and 10 ml of methanol, and the whole was heated to 60° C. for 20 minutes for deformylation. After cooling, 25 ml of additional 35% hydrochloric acid was added, and the whole was stirred for 2 days at 20° C. for crystallization. Then, it was stirred at 5° C. for an additional 3 hours. The crystals precipitated out were isolated to obtain 11.6 g of crude wet α-APM.HCl crystals.

These were analyzed by an amino acid analyzer and high performance liquid chromatography and were found to contain 7.6 g of α-APM, 0.35 g of α-APM2 and 0.48 g of α-AP. Yield of α-APM hydrochloride to F-α-APM was 42%.

Example 3

A mixed solvent comprising 25 g of acetic acid and 100 g of toluene containing 20 g of F-α-APM was concentrated under reduced pressure with the continuous addition of 300 ml of toluene thereto, whereby the acetic acid was removed by distillation almost completely. Afterwards, 20 g of water was added to the mixture, which was then heated to 60° C., stirred for 15 minutes and then left static for 30 minutes to form two separate layers, and the aqueous layer subsequently isolated.

To the aqueous layer were added 7 ml of 35% hydrochloric acid and 7 ml of methanol, and the whole was heated to 60° C. for 20 minutes for deformylation. After cooling, 25 ml of additional 35% hydrochloric acid was added, and the whole was stirred for 2 days at 20° C. for crystallization, and at 5° C. for an additional 3 hours. The crystals precipitated out were isolated to obtain 14.8 g of crude wet α-APM.HCl crystals.

These were analyzed by an amino acid analyzer and high performance liquid chromatography and were found to contain 9.5 g of α-APM, 0.42 g of α-APM2 and 0.58 g of α-AP. The yield of α-APM hydrochloride based on F-o-APM was 52%.

Example 4

A mixed solvent comprising 62 g of acetic acid and 200 g of toluene containing 40 g of F-α-APM and 8.6 g of F-β-APM was concentrated under reduced pressure with the continuous addition of 500 ml of toluene thereto, whereby acetic acid was removed by distillation almost completely. The volume was finally concentrated to 260 ml, then 25 ml of water was added thereto and the mixture heated to 60° C. This was stirred for 15 minutes and then left static for 30 minutes to form two separate layers, and, the aqueous layer subsequently isolated.

To the aqueous layer were added 14 ml of 35% hydrochloric acid and 14 ml of methanol, and deformylation followed by crystallization was carried out in the same manner as in Example 1, providing 47.1 g of crude wet α-APM.HCl crystals.

These were analyzed by an amino acid analyzer and high performance liquid chromatography and were found to contain 29.6 g of α-APM, 1.01 g of α-APM2 and 1.35 g of α-AP. Yield of α-APM hydrochloride based on F-o-APM was 80%.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for preparing α-L-aspartyl-L-phenylalanine methyl ester hydrochloride, which comprises:
    (a) adding water to an organic solvent reaction mixture containing N-formyl-α-L-aspartyl-L-phenylalanine methyl ester to form an aqueous layer and an organic layer, and extracting N-formyl-α-L-aspartyl-L-phenylalanine methyl ester into said aqueous layer, at a temperature of from 40° C. to 80° C.;
    (b) isolating, at a temperature from 40° C. to 80° C., said aqueous layer and deformylating the N-formyl-α-L-aspartyl-L-phenylalanine methyl ester therein by adding hydrochloric acid and methanol to said isolated aqueous layer; and
    (c) crystallizing α-L-aspartyl-L-phenylalanine methyl ester hydrochloride salt crystals out of the mixture obtained in step (b).

2. A method of preparing α-L-aspartyl-L-phenylalanine methyl ester hydrochloride, which comprises:
    (a) adding water to an organic solvent reaction mixture comprising toluene and acetic acid and containing N-formyl-α-L-aspartyl-L-phenylalanine metyl ester, and extracting N-formyl-α-L-aspartyl-L-phenylalanine methyl ester into said aqueous layer, at a temperature of from 40° C. to 80° C;
    (b) isolating, at a temperature from 40° C. to 80° C., said aqueous layer and deformylating the N-formyl-α-L-aspartyl-L-phenylalanine methyl ester therein by adding hydrochloric acid and methanol to said isolated aqueous layer; and
    (c) crystallizing α-L-aspartyl-L-phenylalanine methyl ester hydrochloride salt crystals out of the mixture obtained in step b.

3. The method of claim 2, wherein said organic solvent reaction mixture is prepared by concentration of said toluene/acetic acid solution of N-formyl-α-aspartyl-L-phenylalanine methyl ester so that at least part of said acetic acid is removed therefrom.

4. The method of claims 1, wherein said water is added in an amount of from 30 wt.% to 400 wt.% of said N-formyl-α-L-aspartyl-L-phenylalanine methyl ester contained in said organic solvent reaction mixture.

5. The method of claim 1, wherein said organic solvent reaction mixture contains N-formyl-β-L-aspartyl-L-phenylalanine methyl ester in an amount of from 5 wt.% to 35 wt.% of said N-formyl-α-L-aspartyl-L-phenylalanine methyl ester.

6. The method of claim 1 wherein said temperature is from 55° C. to 65° C.

7. A method for preparing α-L-aspartyl-L-phenylalanine methyl ester hydrochloride, which comprises:
    (a) adding water to an organic solvent reaction mixture comprising at least one member selected from the group consisting of N,N-dimethylformamide, acetic acid, ethylene dichloride, dichloromethane, chloroform, methyl acetate, ethyl acetate, toluene and xylene to form an aqueous layer and an organic layer, and extracting N-formyl-α-L-aspartyl-L-phenylalanine methyl ester into said aqueous layer, at a temperature of from 40° C. to 80° C.;
    (b) isolating, at a temperature from 40° C. to 80° C., said aqueous layer and deformylating the N-formyl-α-L-aspartyl-L-phenylalanine methyl ester therein by adding hydrochloric acid and methanol to said isolated aqueous layer; and
    (c) crystallizing α-L-aspartyl-L-phenylalanine methyl ester hydrochloride salt crystals out of the mixture obtained in step (b).

8. The method of claim 3, wherein said concentrating step is carried out at a pressure of from 10 to 760 Torr and at a temperature of 90° C. or lower.

9. The method of claim 8, wherein said concentrating step is carried out at a pressure of from 10 to 760 Torr at a temperature of 60° C. or lower.

* * * * *